(12) United States Patent
Mishima et al.

(10) Patent No.: US 6,780,173 B2
(45) Date of Patent: Aug. 24, 2004

(54) DISPOSABLE UNDERGARMENT WITH ELASTICALLY STRETCHABLE WINGS

(75) Inventors: Yoshitaka Mishima, Kagawa-ken (JP); Koichiro Tani, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 294 days.

(21) Appl. No.: 09/927,835

(22) Filed: Aug. 10, 2001

(65) Prior Publication Data
US 2002/0022818 A1 Feb. 21, 2002

(30) Foreign Application Priority Data
Aug. 11, 2000 (JP) ........................................ 2000-244460

(51) Int. Cl.$^7$ ................................................ A61F 13/15
(52) U.S. Cl. ................................ 604/385.01; 604/385.3
(58) Field of Search ....................... 604/385.01, 385.04, 604/385.3, 385.24

(56) References Cited

U.S. PATENT DOCUMENTS 5,997,521 A   12/1999  Robles et al.
6,200,299 B1 * 3/2001  Heki .......................... 604/386

FOREIGN PATENT DOCUMENTS

| EP | 0 970 677 A2 | 1/2000 |
|---|---|---|
| JP | 10-328237 | 12/1998 |
| WO | WO 95/19753 | 7/1995 |
| WO | WO 98/55062 | 12/1998 |
| WO | WO 00/28122 | 5/2000 |
| WO | WO 00/37006 | 6/2000 |

OTHER PUBLICATIONS

European search report mailed Feb. 5, 2002.

* cited by examiner

*Primary Examiner*—Michele M Kidwell
(74) *Attorney, Agent, or Firm*—Butzel Long

(57) ABSTRACT

A disposable undergarment includes a pair of elastically stretchable first wings extending outward from transversely opposite side edge portions of a rear waist region, proximal side edge portions of the respective first wings are contiguous to transversely opposite side edge portions of a crotch region. The undergarment further includes a pair of elastically stretchable second wings placed upon the first wings and extending outward from the transversely opposite side edge portions of the rear waist region, proximal side edge portions are not contiguous to the transversely opposite side edge portions of the crotch region. A stretch stress generated in the first wings as the front and rear waist regions are connected to each other is exerted upon the undergarment in a waist-surrounding direction as well as in a thigh-surrounding direction but a stretch stress generated at the same time is exerted upon the article only in the waist-surrounding direction.

2 Claims, 6 Drawing Sheets

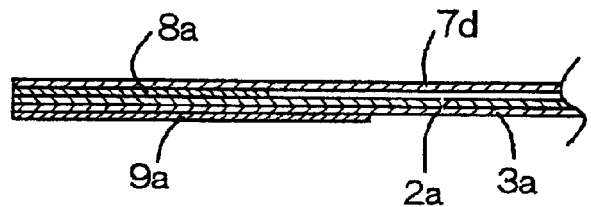
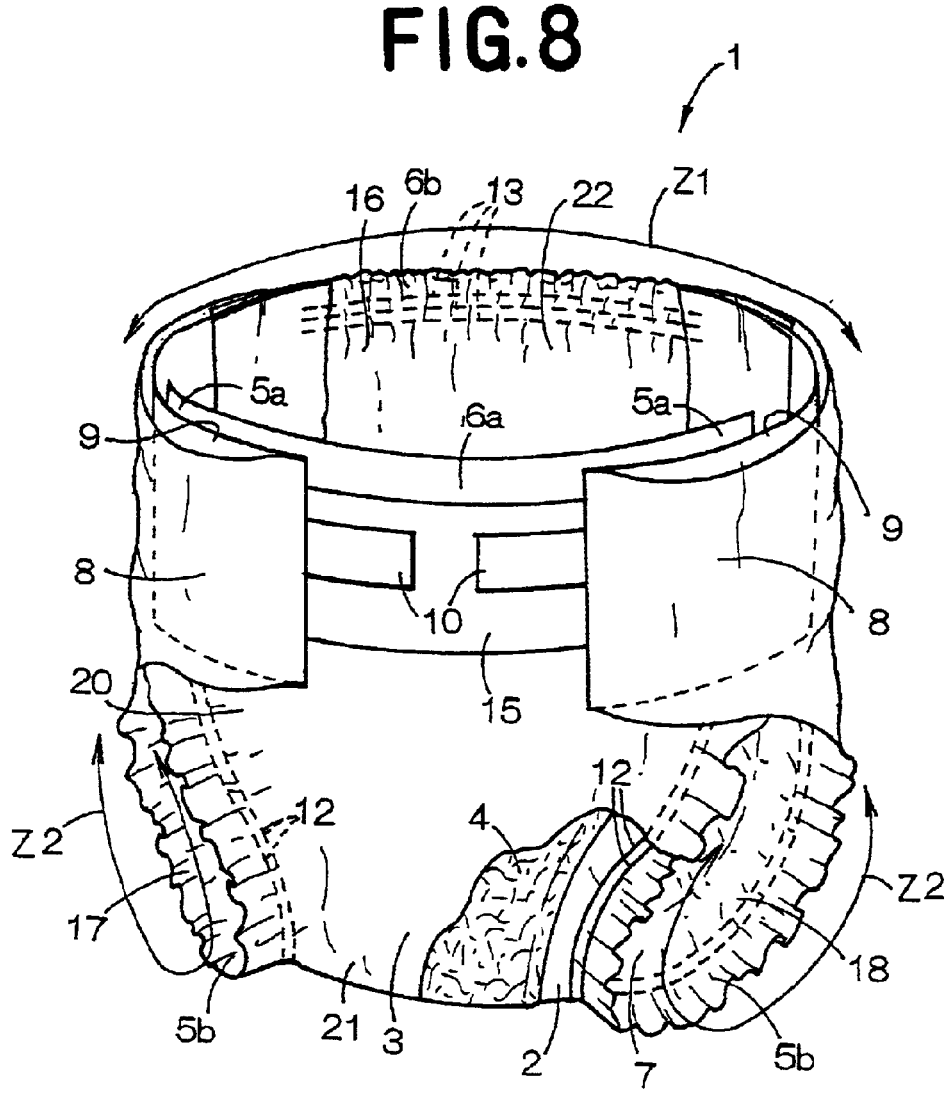

DISPOSABLE UNDERGARMENT WITH ELASTICALLY STRETCHABLE WINGS

BACKGROUND OF THE INVENTION

This invention relates to a disposable undergarment such as a disposable diaper or a diaper cover.

Japanese Patent Application Publication No. 1998-328237A describes a disposable undergarment composed, in its longitudinal direction, of front and rear waist regions and a crotch region extending between these waist regions wherein a pair of wings made of stretchable sheet material extend outward from transversely opposite side edge portions of the rear waist region in a transverse direction of the undergarment and lateral ends of the respective wings are made of elastic material presenting a stretch stress higher than that in the remaining portions. The undergarment disclosed in the Publication comprises a liquid-pervious topsheet, a liquid-impervious backsheet and a liquid-absorbent core disposed between these sheets. Tape fasteners serving to connect the front and rear waist regions are attached to free side edge portions of the respective wings. To put the undergarment on a wearer's body, the wings are stretched in a waist-surrounding direction to engage the tape fasteners with a target tape strip attached to the front waist region and thereby to connect the front and rear waist regions to each other. With the undergarment, the transversely opposite side edge portions of the undergarment in its crotch region are pulled in a thigh-surrounding direction as the wings are stretched in the waist-surrounding direction. In this way, the transversely opposite side edge portions ensure the undergarment to be tightly held around the wearer's thighs.

Depending on a circumferential size of the wearer's thigh, it is sometimes desired for the undergarment such as a disposable diaper or a diaper cover to alleviate a compressive effect of the transversely opposite side edge portions in the crotch region around the wearer's thighs. In the case of the undergarment disclosed in the Publication, this may be achieved by connecting the front and rear waist regions to each other without fully stretching the wings in the waist-surrounding direction. However, this will result in that the undergarment can not be reliably held around the wearer's waist and the undergarment is apt to get out of its proper position.

SUMMARY OF THE INVENTION

It is an object of this invention to provide a disposable undergarment that can be reliably held around a wearer's waist to prevent the undergarment from slipping down without excessively compressing the wearer's thighs.

According to this invention, there is provided a disposable undergarment contoured by transversely opposite side edge portions extending in a longitudinal direction and longitudinally opposite end portions extending in a transverse direction so as to be composed, in the longitudinal direction, of a front waist region, a rear waist region and a crotch region extending between these waist regions, the undergarment having a pair of elastically stretchable first wings extending outward from transversely opposite side edge portions of the front waist region and/or the rear waist region, the first wings having first proximal side edge portions lying on the transversely opposite side edge portions of the waist region and first free side edge portions spaced outward from the first proximal side edge portions in the transverse direction, the first free side edge portions being provided with means to connect the front and rear waist regions to each other wherein the first proximal side edge portions are contiguous to the transversely opposite side edge portions of the crotch region and a stretch stress generated in the first wings as the front and rear waist regions are connected to each other is exerted upon the undergarment in a waist-surrounding direction as well as in a thigh-surrounding direction.

According to this invention a pair of elastically stretchable second wings prepared separately of the undergarment extend outward from the transversely opposite side edge portions of the waist region in the transverse direction so as to be placed upon the first wings, the second wings having second proximal side edge portions lying on the transversely opposite side edge portions of the waist region and second free side edge portions spaced outward from the first proximal side edge portions in the transverse direction and fixed to the first free side edge portions, wherein the second proximal side edge portions are not contiguous to the transversely opposite side edge portions of the crotch region and a stretch stress generated in the second wings as the front and rear waist regions are connected to each other is exerted upon the undergarment in a waist-surrounding direction.

According to one embodiment of this invention, a transverse dimension of the first wing as measured from its first proximal side edge portion to its free side edge portion and a transverse dimension of the second wing as measured from its second proximal side edge portion to its second free side edge portion are in a relationship of the first wing being nearly equal to the second wing or the first wing being greater than the second wing and wherein values of the stretch stress generated in the first and second wings as these first and second wings are stretched outward in the transverse direction are in a relationship of the first wing being less than the second wing.

BRIEF DESCRIPTION OF THE DRAWINGS

FIG. 7 is a sectional view taken along a line D—D in FIG. 5; and

FIG. 8 is a perspective view showing the diaper of FIG. 5 as the front and rear waist regions connected to each other.

DETAILED DESCRIPTION OF THE PREFERRED EMBODIMENTS

Details of a disposable diaper as an example of a disposable undergarment according to this invention will be more fully understood from the description given hereunder with reference to the accompanying drawings.

Figure 1:
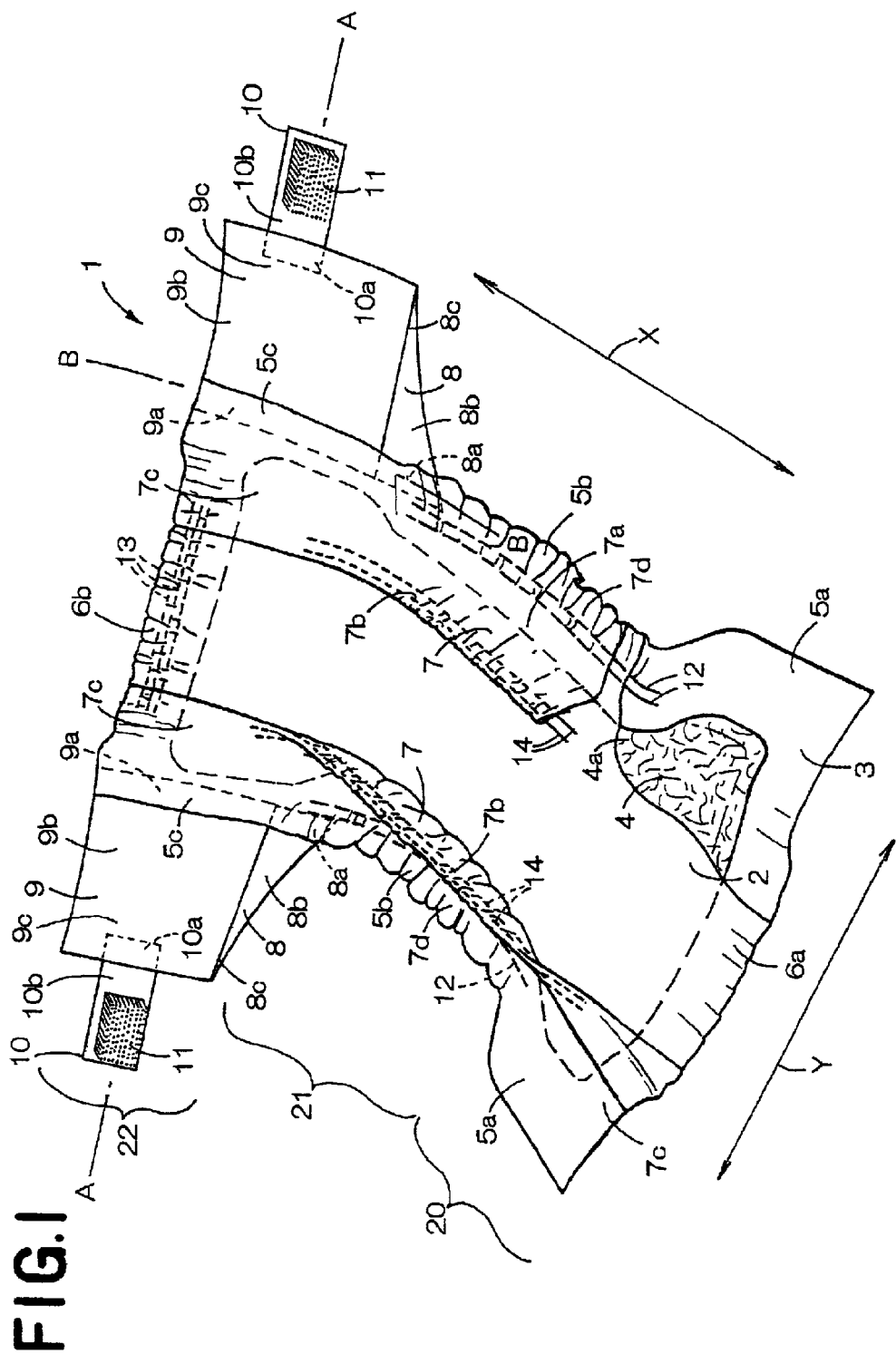
FIG. 1 is a perspective view showing a disposable diaper as partially broken away.
Figure 2:
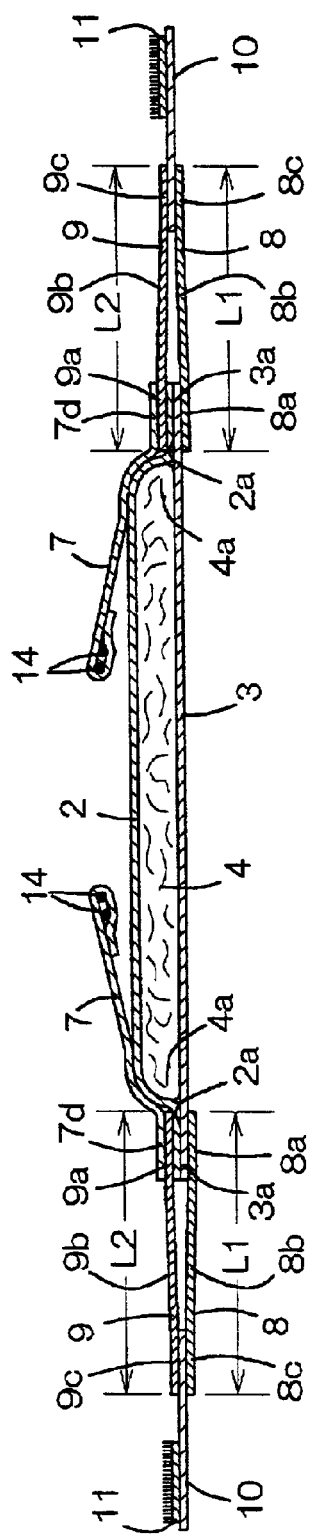
FIG. 2 is a sectional view taken along a line A—A in FIG. 1.
Figure 3:
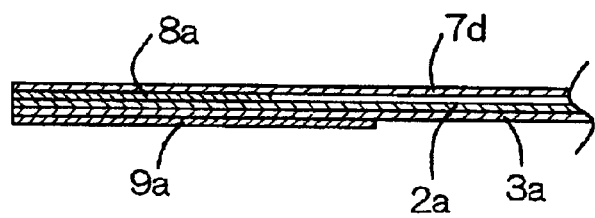
FIG. 3 is a sectional view taken along a line B—B in FIG. 1.

FIG. 1 is a perspective view showing a disposable diaper 1 as partially broken away, FIG. 2 is a sectional view taken along a line A—A in FIG. 1 and FIG. 3 is a sectional view taken along a line B—B in FIG. 1. Referring to FIG. 1, a longitudinal direction is indicated by an arrow X and a transverse direction is indicated by an arrow Y. It should be understood that "inner surfaces" of respective members such as top- and backsheets 2, 3, first and second wings 8, 9, leak-barrier sheets 7 and tape fasteners are those facing a core 4 and "outer surfaces" of them are those not facing the core 4.

The diaper 1 basically comprises a liquid-pervious topsheet 2, a liquid-impervious backsheet 3 and a liquid-absorbent core 4 disposed between said top- and backsheets 2, 3 and entirely covered with and bonded to water-pervious tissue paper (not shown). The core 4 is bonded to at least one of the inner surfaces of the top- and backsheets 2, 3 with the tissue paper therebetween.

The diaper 1 is composed, in the longitudinal direction, of a front waist region 20, a rear waist region 22 and a crotch region 21 extending between the front and rear waist regions 20, 22 and has transversely opposite side edge portions 5a, 5b, 5c extending in the longitudinal direction and longitudinally opposite end portions 6a, 6b extending in the transverse direction.

The diaper 1 is provided with a pair of leak-barrier sheets 7 extending in the longitudinal direction outside transversely opposite side edges of the core 4 and provided in the rear waist region 22 with respective pairs of first and second wings 8, 9 extending transversely outward from the side edge portions 5c. In this diaper 1, the side edge portions 5a in the front waist region 20 extend transversely outward further than the side edge portions 5b in the crotch region 21 so that the diaper 1 presents a hourglass-like shape in its plan view.

Each of the first wings 8 has a substantially rectangular shape and formed from an elastically stretchable sheet. Specifically, the first wing 8 has a first proximal side edge portion 8a lying on the side edge portions 5c of the rear waist region 22 and extending in the longitudinal direction, a first free side edge portion 8c spaced apart from the proximal side edge portion 8a in the transverse direction and extending in the longitudinal direction, and an intermediate portion 8b lying between the proximal side edge portion Sa and the free side edge portion 8c. The proximal side edge portion 8a is continuous to the side edge portion 5b of the diaper 1 in the crotch region 21.

Each of the second wings 9 is formed from an elastically stretchable sheet and presents a substantially rectangular shape. The second wing 9 lies on and is placed upon the inner surface of the first wing 8. More specifically, the second wing 9 has a second proximal side edge portion 9a lying on the side edge portions 5c of the rear waist region 22 and extending in the longitudinal direction, a second free side edge portion 9c spaced apart from the proximal side edge portion 9a in the transverse direction and extending in the longitudinal direction, and an intermediate portion 9b lying between the proximal side edge portion 9a and the free side edge portion 9c. The second wing 9 is different from the first wing 8 in that proximal side edge portion 9a is not continuous to the side edge portion 5b of the diaper 1 in the crotch region 21.

The first and second wings 8, 9 at each side have their free side edge portions 8a, 9a bonded together. A transverse dimension L1 as measured from the outermost edge of the proximal side edge portion 8a to the outermost edge of the free side edge portion 8c in the wing 8 is equal to a transverse dimension L2 as measured from the outermost edge of the proximal side edge portion 9a to the outermost edge of the free side edge portion 9c. Strictly to describe, regarding these transverse dimensions L1, L2, the first and second wings 8, 9 may be in a relationship of the first wing 8≈second wing 9.

Tape fasteners 10 are attached to the free side edge portions 8c, 9c of the first and second wings 8, 9, respectively. Each of the tape fasteners 10 has a proximal end portion 10a and a free end portion 10b extending outward from said proximal end portion 10a in the transverse direction. The free end portion 10b is provided on its inner surface with a hook member 11 as a component of the so-called mechanical fastener.

Each of the leak-barrier sheets 7 has a fixed side edge portion 7a fixed to the topsheet 2, a free side edge portion 7b extending in parallel to the fixed side edge portion 7a and longitudinally opposite end portions 7c collapsed inward in the transverse direction of the diaper 1 and bonded to the topsheet 2 in such collapsed state. The leak-barrier sheet 7 further includes an outer side portion 7d extending outward from the fixed side edge portion 7a in the transverse direction. An elastically stretchable member 14 extending in the longitudinal direction is bonded under tension to the free side edge portion 7b. The elastic member 14 is covered with a part of the free side edge portion 7b.

An elastically stretchable member 12 comprising a plurality of elastic elements and extending in the longitudinal direction is attached under tension to each of the transversely opposite side edge portions 5b so as to be associated with each of the leg-openings. The elastic member 12 associated with the leg-opening is disposed between the top- and backsheets 2, 3 and bonded to the inner surface of at least one of these sheets 2, 3.

An elastically stretchable member 13 comprising a plurality of elastic elements and extending in the transverse direction is attached under tension to each of the longitudinally opposite end portions 6b so as to be associated with a waist-opening. The elastic member 13 associated with the waist-opening is disposed between the top- and backsheets 2, 3 and bonded to the inner surface of at least one of these sheets 2, 3.

Along the transversely opposite side edge portions 5c, transversely opposite side edge portions 2a, 3a of the top- and backsheets 2, 3 and the outer side portions 7d of the respective leak-barrier sheets 7 extend outward from the transversely opposite side edges 4a of the core 4 and the proximal side edge portions 8a of the first wings 8 are bonded to the outer surface of the side edge portions 3a of the backsheet 3. The proximal side edge portions 9a of the second wings 9 are disposed between and bonded to the respective side edge portions 2a of the topsheet 2 and the respective outer side portions 7d of the leak-barrier sheets 7. The tape fasteners 10 have the proximal end portions 10a thereof disposed between the respective free side edge potions 8c, 9c of the first and second wings 8, 9 and bonded to the inner surfaces of these wings 8, 9.

Along the transversely opposite side edge portions 5a, 5b, the transversely opposite side edge portions 2a of the topsheet 2 are disposed between and bonded to the transversely opposite side edge portions 3a of the backsheet 3 and the respective outer side portions 7d of the leak-proof sheets 7.

Referring to FIG. 1, the transversely opposite side edge portions 5b as well as the longitudinally opposite end portions 6b of the diaper 1 and the free side edge portions 7b of the leak-barrier sheets 7 are formed with a plurality of gathers as the respective elastic members 12, 13, 14 contract. Thereupon, the topsheet 2 is curved in the longitudinal direction with the topsheet 2 inside and contraction of the elastic member 14 causes the free side edge portions 7b of the respective leak-barrier sheets 7 to rise upward as viewed in FIG. 1.

Figure 4:
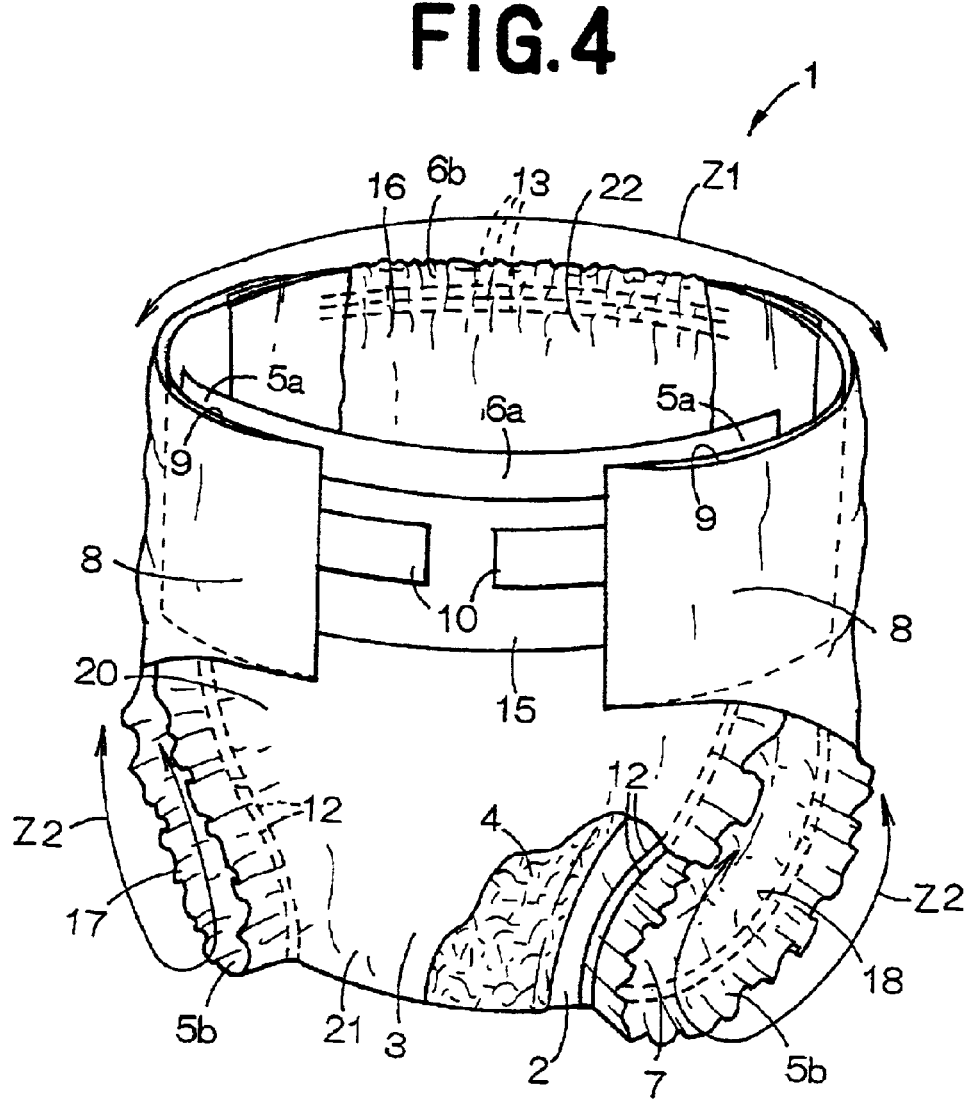
FIG. 4 is a perspective view showing the diaper of FIG. 1 with the front and rear waist regions connected to each other.

FIG. 4 is a perspective view showing the diaper 1 with the front and rear waist regions 20, 22 connected to each other, in which a waist-surrounding direction is indicated by an arrow Z1 and a thigh-surrounding direction is indicated by an arrow Z2. To connect the front and rear waist regions 20,22 to each other, the first and second wings 8,9 are stretched in the waist-surrounding direction and placed upon the respective side edge portions 5a of the diaper 1. Then, the respective hook members 11 of the tape fasteners 10 are engaged with a loop member 15 attached to the outer surface of the backsheet 3 in the front waist region. By connection the front and rear waist regions 20,22 to each other in this manner, a waist-opening 16 and a pair of leg-openings 17,18 are defined.

The end portion 6b is pulled by the first wings 8 in the waist-surrounding direction and the transversely opposite side edge portions 5b are pulled in the thigh-surrounding direction as the first wings 8 are stretched in the waist-surrounding direction since the proximal side edge portions 8a of the first wings 8 are connected to the transversely opposite side edge portions 5b. A stretch stress of the first wings 8 is exerted upon the diaper 1 in the waist-surrounding direction as well as in the thigh-surrounding direction.

The end portion 6b of the diaper 1 is pulled by the second wings 8 in the waist-surrounding direction as the second wings 9 are stretched in the waist-surrounding direction. However, the transversely opposite side edge portions 5b are not pulled in the thigh-surrounding direction since the proximal side edge portions 9a of the second wings 9 are not connected to the transversely opposite side edge portions 5b of the diaper 1. A stretch stress of the second wings 9 is exerted upon the diaper 1 only in the waist-surrounding direction.

The stretch stress of both the first wings 8 and the second wings 9 is exerted upon the diaper 1 at least in the waist surrounding direction so that a desired fitness of the diaper 1 around the wearer is waist is ensured by the first and second wings 8, 9 and the end portion 6b. On the other hand, the stretch stress of the second wings 9 is not exerted upon the diaper 1 in the thigh-surrounding direction so that an undesirable pressure exerted by the transversely opposite side edge portions 5b around the wearer's thighs can be appropriately alleviated in comparison with the case in which the stretch stress of the second wings 9 is exerted upon the diaper 1 in the thigh-surrounding direction also.

An arrangement is also possible in which respective values of stretch stress generated in the first and second wings 8, 9 as these wings 8, 9 are stretched outward in the transverse direction to the same length are in a relationship of the first wings 8<the second wings 9. By adjusting the stretch stress of the second wings 9 higher than that of the first wings 8, the diaper 1 can be further tightly placed around the wearer's waist.

Figure 5:
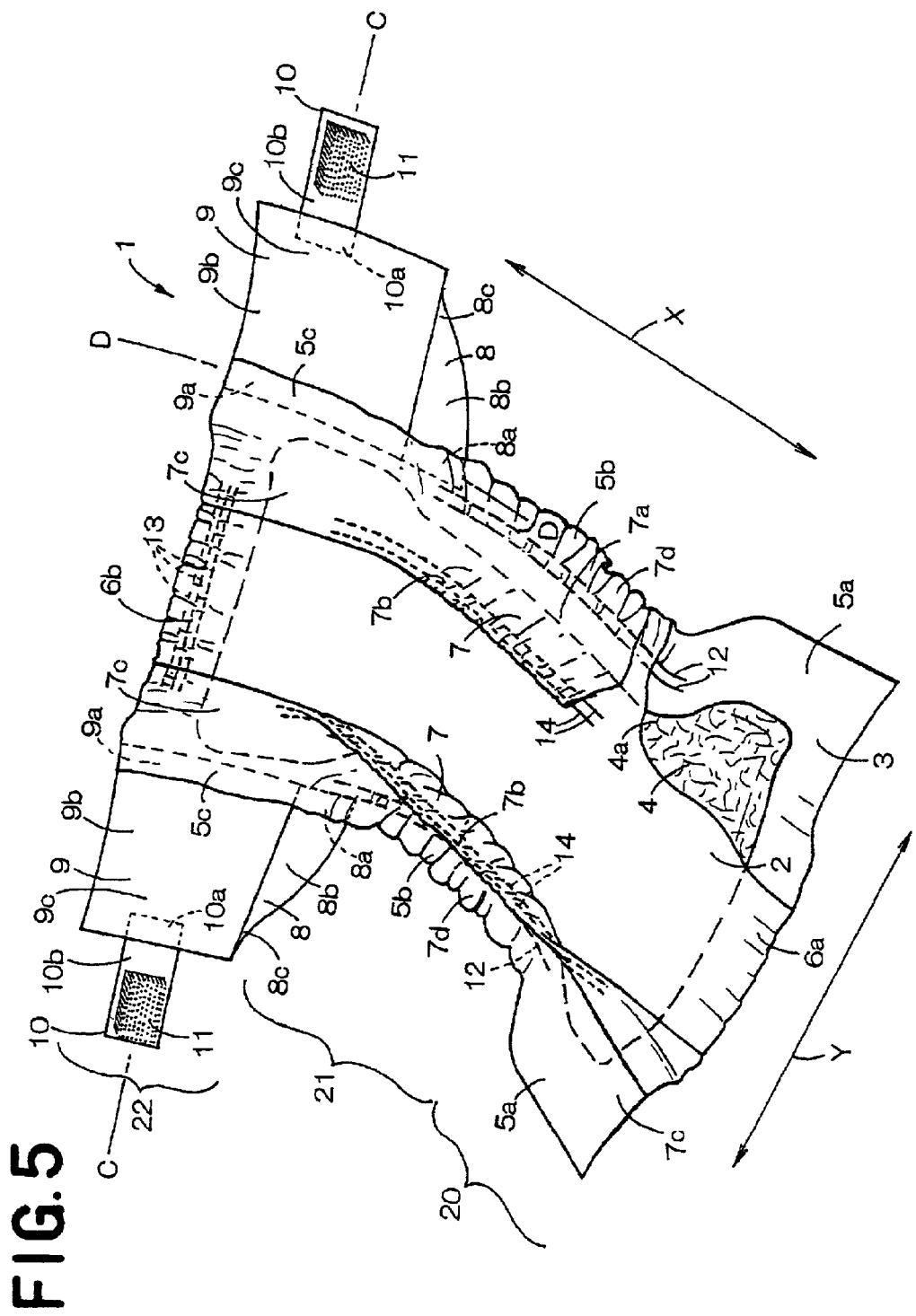
FIG. 5 is a perspective view showing the disposable diaper according to another embodiment of this invention as partially broken away.
Figure 6:
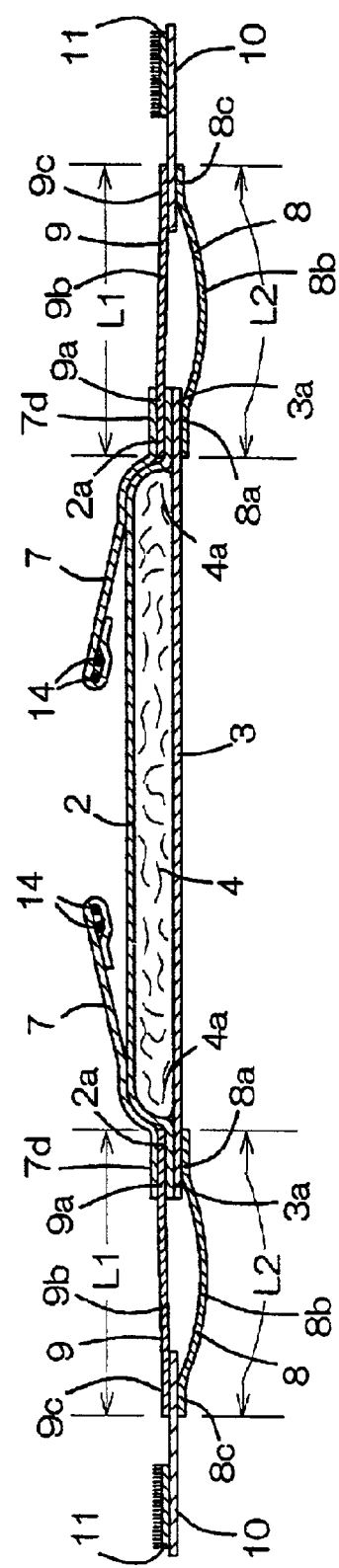
FIG. 6 is a sectional view taken along a line C—C in FIG. 1.

FIG. 5 is a perspective view showing another embodiment of the disposable diaper 1 as partially broken away, FIG. 6 is a sectional view taken along a line C—C in FIG. 5 and FIG. 7 is a sectional view taken along a line D—D in FIG. 5. Referring to FIG. 5, a longitudinal direction is indicated by an arrow X and a transverse direction is indicated by an arrow Y. The diaper 1 according to this embodiment is basically similar to the diaper of FIG. 1 and therefore description of this embodiment will be limited to features different from those of the diaper 1 illustrated in FIG. 1.

In the case of this diaper 1, the transverse dimension L1 as measured from the outermost edge of the proximal side edge portion 8a to the outermost edge of the free side edge portion 8c in the first wing 8 and the corresponding dimension L2 from the outermost edge of the proximal side edge portion 9a to the outermost edge of the free side edge portion 9c in the second wing 9 are in a relationship of the first wing 8>the second wing 9. Regarding the stretch stress per unit area, a relationship of the first wing≈the second wing 9 is established.

FIG. 8 is a perspective view showing the diaper 1 with the front and rear waist region 20, 22 connected to each other, in which a waist-surrounding direction is indicated by an arrow Z1 and a thigh-surrounding direction is indicated by an arrow Z2. Similar to the case shown in FIG. 4, a stretch stress of the first wings 8 is exerted upon the diaper 1 in the waist-surrounding direction as well as in the thigh-surrounding direction and a stretch stress of the second wings 9 is exerted upon the diaper 1 in the waist-surrounding direction.

While values of stretch stress per unit area generated in the first and second wings 8, 9 are substantially the same, the dimension L2 of the second wing 9 is smaller than the dimension L1 of the first wing 8. Consequently, the stretch stress is generated substantially higher in the second wing 8 than in the first wing 9 as these wings 8, 9 are stretched outward in the transverse direction to the same length. The diaper 1 according to this embodiment also ensures that the second wings 9 cooperate with the end portion 6b to place the diaper 1 tightly around the wearer's waist as the first and second wings 8, 9 are stretched in the waist-surrounding direction in order to connect the front and rear waist regions 20, 22 to each other.

Referring to FIG. 7, the transverse dimension of the first wing 8 as measured from its proximal side edge portion 8a to its free side edge portion 8c and the corresponding dimension of the second wing 9 from its proximal side edge portion 9a to its free side edge portion 9c may be in a relationship of the first wing 8>the second wing 9. Regarding the stretch stress per unit area, it is also optional to establish a relationship of the first wing 8<the second wing 9.

In the diaper 1 according to both embodiments, it is also possible without departing from the scope of this invention to attach the first and second wings 8, 9 to the transversely opposite side edge portions 5a of the diaper 1 in the front waist region 20. It is also possible to form the first wings 8 from the backsheet 3. In this case, a laminated sheet consisting of a hydrophobic nonwoven fabric having an elastic stretchability and plastic film having an elastic stretchability is preferably used as the backsheet 3 which is, in turn, intermittently bonded under tension in the longitudinal direction as well as in the transverse direction to the topsheet 2 in their portions placed upon each other.

The topsheet 2 may be formed from a liquid-pervious sheet such as a nonwoven fabric or porous plastic film, preferably from a liquid-pervious hydrophilic sheet. The backsheet 3 may be formed from a hydrophobic nonwoven fabric, liquid-impervious plastic film or a laminated sheet of hydrophobic nonwoven fabric and plastic film, preferably from a breathable but liquid-impervious sheet.

The first and second wings 8,9 may be formed from a nonwoven fabric or plastic film both being elastically stretchable or a laminated sheet consisting of such nonwoven fabric and plastic film. The leak-barrier sheets 7 may be formed from a hydrophobic nonwoven fabric.

The nonwoven fabric may be selected from a group including spun lace-, needle punch-, melt blown-, thermal bond-, spun bond-, chemical bond- and air through-nonwoven fabric. Component fiber of the nonwoven fabric may be selected from a group including polyolefine-, polyester- and polyamide-based fibers and polyethylene/polypropylene or polyethylene/polyester core-sheath type conjugated fiber and side-by-side-type conjugated fiber.

The core 4 is a mixture of fluff pulp, high absorption polymer grains and thermoplastic synthetic resin fiber compressed to a desired thickness. The high absorption polymer may be selected from a group including starch-, cellulose-based polymer and synthetic polymer.

Bonding of the top- and backsheets 2, 3, the first and second wings 8, 9, the leak-barrier sheets 7, the core 4 as well as attaching of the elastic member 12, 13, 14 may be carried out using suitable adhesive such as a hot melt adhesive agent or a technique of welding.

This invention is applicable not only to the disposable diaper but also to a diaper cover.

The disposable undergarment according to this invention advantageously has a unique arrangement such that a stretch stress generated in the first wings as the first and second wings are stretched in the waist-surrounding direction in order to connect the front and rear waist regions to each other is exerted upon the diaper in the waist-surrounding direction as well as in the thigh-surrounding direction. On the other hand, a stretch stress generated at the same time in the second wings is exerted upon the diaper only in the waist-surrounding direction. As a result, a possibly excessive pressure exerted by the transversely opposite side edge portions of the undergarment in the crotch region around the wearer's thighs can be appropriately alleviated while a sufficient fitness of the undergarment around the wearer's waist is ensured to prevent the undergarment from slipping down along the wearer's waist.

With the undergarment arranged so that the stretch stress generated in the second wings is higher than that generated in the first wings, the second wings further reliably hold the undergarment around the wearer's waist and thus prevent the undergarment from getting out of its proper position.

With the undergarment arranged so that the transverse dimension of the second wing as measured from its proximal side edge portion to its free side edge portion is smaller than the corresponding dimension of the first wing and the stretch stress per unit area generated in the first and second wings is substantially same, the stretch stress generated in the second wing is substantially higher than that generated in the first wing as the first and second wings are stretched outward in the transverse direction. In a consequence, for the undergarment of such arrangement also, the undergarment can be further reliably held by the second wings around the wearer's waist and the effect to prevent the undergarment from getting out of its proper position can be thereby achieved.

What is claimed is:

1. A disposable undergarment comprising:

transversely opposite side edge portions extending in a longitudinal direction;

longitudinally apposite end portions extending in a transverse direction;

a front waist region;

a rear waist region;

a crotch region extending between said front waist region and said rear waist region in said longitudinal direction;

a pair of elastically stretchable first wings extending outward from transversely opposite side edge portions of at least one of said front waist region and said rear waist region, said first wings having first proximal side edge portions lying on said transversely opposite side edge portion of said waist region and first free side edge portion spaced outwardly from said first proximal side edge portion in said transverse direction, said first free side edge portions being providing with means to connect said front and rear waist regions to each other, said first proximal side edge portions being contiguous to said transversely opposite side edge portions of said crotch region and a stretch stress generated in said first wings as said front and rear waist regions are connected to each other is exerted upon said undergarment in a waist-surrounding direction as well as in a thigh-surrounding direction; and a pair of elastically stretchable second wings extending outward from said transversely opposite side edge portions of said waist region in said transverse direction, said second wings being placed upon said first wings so that longitudinal upper ends of said first wings and longitudinal upper ends of said second wings coextensively overlap each other, said second wings having second proximal side edge portions lying on said transversely opposite side edge portions of said waist region and second free edge portions spaced outward from said second proximal side edge portions in said transverse direction and fixed to said first free side edge portions, said second proximal side edge portions being non-contiguous to said transversely opposite side edge portions of said crotch region, and a stretch stress generated in said second wings as said front and rear waist regions are connected to each other is exerted upon said undergarment in a waist-surrounding direction.

2. The undergarment according to claim 1, wherein a transverse dimension D1 of said first wings as measured from first proximal side edge portions thereof to first free side edge portions thereof and a transverse dimension D2 of said second wings as measured from second proximal side edge portions to second free side edge are in a relationship of D1 being greater than or equal to D2, and values of said stretch stress generated in said first and second wings as these first and second wings are stretched outward in aid transverse direction are in a relationship of the values of said stretch stress of said first wing being less that values of said stretch stress of said second wing.

* * * * *